US007179635B2

(12) United States Patent
Haaland et al.

(10) Patent No.: US 7,179,635 B2
(45) Date of Patent: Feb. 20, 2007

(54) PEPTIDES FOR USE IN CULTURE MEDIA

(75) Inventors: Perry D. Haaland, Chapel Hill, NC (US); Douglas B. Sherman, Durham, NC (US); Robert L. Campbell, Bahama, NC (US); Walter William Stewart, Cary, NC (US); Sheila A. Lloyd, Cary, NC (US); Bruce Wayne Erickson, deceased, late of Chapel Hill, NC (US); by Ann Hart Erickson, legal representative, Chapel Hill, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 41 days.

(21) Appl. No.: 10/841,121

(22) Filed: May 7, 2004

(65) Prior Publication Data

US 2004/0265911 A1    Dec. 30, 2004

Related U.S. Application Data

(62) Division of application No. 09/608,892, filed on Jun. 30, 2000, now Pat. No. 6,759,510.

(51) Int. Cl.
*C12N 1/20* (2006.01)
(52) U.S. Cl. ............... 435/252.7; 435/252.1; 435/244; 435/243; 435/410; 435/325; 530/330
(58) Field of Classification Search ........... 435/252.7, 435/252.1, 244, 243, 410, 325; 530/330
See application file for complete search history.

(56) References Cited

U.S. PATENT DOCUMENTS 5,464,819 A * 11/1995 Suzuki .................. 514/16
5,556,762 A    9/1996 Pinilla et al.
6,103,871 A    8/2000 Wei et al.
6,759,510 B1   7/2004 Haaland et al.
2003/0165808 A1* 9/2003 Campbell et al. ............ 435/4

FOREIGN PATENT DOCUMENTS

| WO | WO 86/00991 | 2/1986 |
| WO | WO 95/09868 | 4/1995 |
| WO | WO 96/01643 | 1/1996 |

OTHER PUBLICATIONS

Cho et al., J. Chem. Inf. Comput. Sci., 1998, 259-268.
Desmazeaud et al., Eur. J. Biochem., 28, 190-198 (1972).
Desmazeaud et al., Biochimie, 1973, 55, 679-684.
Poch et al., J. Agric. Food Chem., 1991, 39, 73-77.
Bezkorovalny, Amer. J. of Clinical Nutrition, 32, Jul. 1979, 1428-1432.
Azuma et al., Agric. Biol. Chem., 48 (8), 2159-2162, 1984.
Azuma et al., Agric. Biol. Chem. 53 (19), 2631-2634, 1989.
Saha et al., 1989, Acta Virol. 33, 338-343.
Wilk, et al., Purification, Characterization, and Cloning of a Cytosolic Aspartyl Aminopeptidase, The Journal of Biological Chemistry, vol. 273, No. 26, Issue of Jun. 26, pp. 15961-15970, 1998, The American Society of Biochemistry and Molecular Biology, Inc.

* cited by examiner

*Primary Examiner*—T. D. Wessendorf
(74) *Attorney, Agent, or Firm*—Alston & Bird LLP

(57) ABSTRACT

The present invention provides peptides libraries which are useful for rapid identification of biologically active compounds. The invention further provides peptides which include cell-growth affecting peptides and peptides which enhance or inhibit production of cellular proteins. Many of the peptides of the invention may be produced in large quantity by recombinant techniques and formulated in culture medium to produce the desired effect on cultured cells and tissues. Certain of the libraries of the invention and the peptides identified in them are particularly useful in concatemer-based recombinant expression methods.

15 Claims, No Drawings

PEPTIDES FOR USE IN CULTURE MEDIA

CROSS-REFERENCE TO RELATED APPLICATION

This application is a divisional of U.S. Ser. No. 09/608,892, filed Jun. 30, 2000, now U.S. Pat. No. 6,759,510.

FIELD OF THE INVENTION

The invention relates to peptides which affect cells in culture and to methods for discovery and manufacture of such peptides. In particular, the invention relates to peptides which affect growth of cells in culture and peptides which affect cellular protein production.

BACKGROUND OF THE INVENTION

Tissue and protein hydrolysates have been routinely used as a source of peptides in cell culture media since the late 1800's. They are the most common undefined culture media component in present use in bacteriology and often replace serum in mammalian culture (S. Saha and A. Sen. 1989. *Acta Virol.* 33:338–343). Hydrolysates and serum are not optimal sources of peptides for culture media, however, because their compositions are undefined and variable, and serum may harbor pathogens such as BSE.

It has been recognized that peptides are generally preferred nutrients as compared to their constituent amino acids. Several approaches have been taken in an effort to determine which specific peptides are utilized by a cell culture as a means for identifying defined peptides which affect growth or some other biological activity. A common practice is to analyze spent media in an attempt to identify compounds which have been consumed during culture. This seldom leads to a single compound which can be isolated and studied. The spent media approach cannot identify compounds which affect the cell and are not removed from the medium (e.g., signaling compounds). In an alternative approach, specific proteins are digested and the HPLC-purified peptide fragments are spiked back into the medium to evaluate their effects. This approach may identify a peptide which performs better than the whole protein digest or tissue digest, but the number of possible peptides for analysis is limited. For example, it has been reported that casein hydrolyzed by the neutral protease of *Micrococcus caseolyticus* (M. J. Desmazeaud and J. H. Hermier. 1972. *Eur. J. Biochem.* 28:190–198) and a papain digest of glucagon (M. J. Desmazeaud and J. H. Hermier. 1973. *Biochimie* 55:679–684) enhance the growth of *Streptococcus thermophilus*. In this case the stimulatory peptides were isolated and characterized. It has also been found that trypsin digested K-casein enhances the growth of the genus *Bifidobacterium* (M. Poch and A. Bezkorovainy. 1991. *J. Agric. Food Chem.* 39:73–77), however, the specific peptides which produce this result were not identified. Azuma, et al. (1984. *Agric. Biol. Chem.* 48:2159–2162) and Bezkorovainy, et al. (1979. *Am. J. Clin. Nutr.* 32:1428–1432) reported that a glycopolypeptide derived from enzyme-digested human casein promotes growth of *Lactobacillus bifidus*. Tryptic fragments of human β-casein have also been reported to stimulate DNA synthesis in BALB/c3T3 cells (N. Azuma, et al. 1989. *Agric. Biol. Chem.* 53:2631–2634). The sequences of two such tryptic fragments were determined. These prior art methods are time consuming and have resulted in identification of only a few peptides which generate marginal improvements. Their success has primarily been limited by the raw materials, which are restricted by the starting substrates and the digesting agents used in their preparation.

More recently, developments in peptide synthesis technology have made it at least plausible to prepare and screen large numbers of compounds for media enhancement, either as individual defined sequences or as a mixture of variable sequences in a peptide library. Many of these sequences would not be present or detected in the traditional undefined materials. The library approach has provided an opportunity to screen more peptide sequences for desired biological effects in cell culture, but the primary methods have major disadvantages. Assaying compounds individually means screening millions of samples containing randomly-generated sequences. As a practical matter, the exhaustive synthesis and screening of libraries is often prohibitively expensive and also time-consuming. The combinatorial approach runs the risk of missing potential lead compounds due to poor representation (low concentration) of each compound in the cocktail due to solubility restraints and masking effects that can occur from competing compounds. In an effort to reduce the number of sequences which must be screened in a library, practitioners have "fixed" certain residue positions during synthesis of the library. That is, certain residues at certain positions in the sequence are added randomly, but the residues at other positions are defined. Such a synthetic peptide library is described in U.S. Pat. No. 5,556,762. In addition, Geysen (WO 86/00991) describes libraries comprising peptide sequences which are a combination of defined and undefined amino acid residues. Furka, et al. (1988. $14^{th}$ *Int Cong. Biochem.* Vol. 5, Abst. FR:013) discloses relatively simple mixtures of tetrapeptides in which the N- and C-terminal residues are fixed and any one of three residues occur at each position in between. Fodor, et al. (1991. *Science* 251:767–773) teach solid phase peptide synthesis on slides, using predetermined amino acids coupled to defined areas of the slide using photomasks. In this way an array of 1024 different peptides with defined C-termini was synthesized. All of these techniques attempt to circumvent the individual screening of millions of peptides and to increase the amount of a given sequence in the library to simplify screening and identification of biologically active peptides.

While fixed-position (i.e., limited diversity) libraries reduce the number of sequences which must be screened, they also limit the number of different sequences available for screening and thus may reduce the probability of identifying a sequence with the desired properties. In the publications discussed above, there was typically no attempt made to "re-expand" the number of available sequences in order to identify additional sequences which may have properties similar to those in the limited diversity library. Recently, information about the properties of a compound identified in a more limited library of sequences has been used to generate a more diverse library of compounds which are structurally similar to the initial compound identified. These additional compounds, which were not present in the initial library, may exhibit biological activities which are similar to the initial lead compound. This approach is often referred to as rational design of targeted libraries. See, for example, S. Cho, et al. 1998. *J. Chem. Inf. Comput. Sci.* 38:259–268.

For media applications, simply identifying a compound delivering the desired enhancement is not sufficient. To impact the overall media optimization process, a lead compound must be rapidly scaled up and made available in a time frame which will impact the typical media optimization cycle. Further, the method used for the initial scale up must be in-line with the planned commercial manufacturing process capable of delivering the compound at a cost in-line with benefit. The ideal discovery process would link the initial library design to the preferred manufacturing process and thereby avoid a series of subsequent libraries aimed at finding compounds with similar performance attributes that can also be manufactured. None of the existing fixed-library designs address this need. Indeed, the manufacturing aspect is left to chance.

There is therefore a need in the art for chemically-defined peptides with well-characterized biological activities which can be added to culture media to produce a desired biological effect. Such peptides reduce the number and quantity of undefined components in culture media, reduce the need for animal-derived components, improve media consistency and quality control and provide a means for precisely controlling and adjusting performance of the cell culture. The present invention employs a peptide library approach to select and identify peptides which meet these needs, in particular a process that links discovery and manufacturing of peptides which affect cell growth (either positively or negatively) or which enhance or inhibit cellular protein production.

SUMMARY OF THE INVENTION

The present invention provides peptide libraries which are useful for rapid identification of biologically active compounds which affect the properties of cells in culture. The present invention further provides peptides identified in these libraries, which include cell growth enhancing peptides, cell growth inhibiting peptides and peptides which enhance or inhibit production of cellular proteins, particularly production of β-toxin by *Clostridium perfringens*. Once the sequence of a peptide having the desired biological activity is identified, it may be produced in large quantity (e.g., by chemical synthesis or expression of recombinant DNA) and formulated in a culture medium to produce the desired effect on cultured cells. The libraries of the invention and the peptides identified in them are particularly useful in certain large-scale, economical recombinant production methods.

DETAILED DESCRIPTION OF THE INVENTION

A limited diversity peptide library was constructed using conventional techniques for peptide synthesis and was subsequently screened for biologically active peptides exhibiting certain desired characteristics. The initial goal was to identify peptides which could be included in culture media to increase the amount of β-toxin produced by *C. perfringens*, either by increasing cell growth (i.e., cell number) or by increasing the amount of toxin produced per cell. The library of initial candidates was based on several design criteria. First, it is known that proteose peptone is a preferred hydrolysate for culturing *C. perfringens*. Proteose peptone is manufactured using pepsin, so leucine would be one of the more common C-termini in the peptides of the hydrolysate. Accordingly, a tetrapeptide library was constructed with leucine as the C-terminus (the fourth position of the peptide) and alanine (a simple amino acid) in the third position as a spacer. The ten Selected Amino Acid Group Representatives shown below, each representing a group of related amino acids, were selected for insertion at the remaining first two positions of the peptides. Selection of the group representative amino acid is typically based on ease of peptide synthesis using that amino acid.

| Cluster Group | Selected Amino Acid Group Representative | Alternative Group Representative |
|---|---|---|
| Acid | Glu (E) | Asp (D) |
| Amide | Gln (Q) | Asn (N) |
| Hydroxy Aliphatic | Ser (S) | Thr (T) |
| Small Aliphatic | Ala (A) | |
| Beta Aliphatic | Val (V) | Ile (I) |
| Large Aliphatic | Leu (L) | Met (M) |
| Aromatics | Phe (F) | Tyr (Y) |
| | | Trp (W) |
| Basic | Lys (K) | Arg (R) |
| Other | Pro (P) | His (H) |
| | Gly (G) | Cys (C) |

These ten amino acids were substituted in each of the first two positions, resulting in a limited diversity library consisting of 100 different tetramer sequences. This library is referred to as the XXAL library, with "X" indicating an amino acid selected to represent a cluster group. Peptides for the peptide library may be synthesized by any suitable method known in the art, such as FMOC chemistry of Atherton and Sheppard (1989) in solid phase peptide synthesis (Merrifield, 1965). Boc chemistry may also be used as well as synthesis on a variety of different solid supports, "tea-bag" synthesis (Houghten), and split and divide combinatorial methods. Solution phase methods for peptide synthesis may also be used. The library peptides may include modifications to the C-terminus (e.g., amides and esters), the N-terminus (e.g., acetyl) and non-naturally occurring amino acids (e.g., norleucine) to assess the effect of such modifications on peptide activity.

To identify peptides in the library which positively or negatively affect cell growth in culture, the library is screened in a growth assay. The selected cells are first grown in appropriate culture media without peptide supplement, then subcultured in media supplemented with each of the library peptides. The screening medium may be a complex medium for the selected cell type, but is preferably a defined medium to allow evaluation of peptide effects without interference from undefined materials present in the medium. It is also preferable to optimize the base medium for cell growth prior to peptide screening, although unoptimized media may also be used. In the present work, growth of *C. perfringens* in the presence and absence of the peptides was evaluated in a basal medium rich in amino acids and containing the necessary vitamins, metals, and simple carbon source. However, selection of an appropriate medium for growth screening of other cell types is routine and within the skill in the art. After an appropriate incubation time, growth of each peptide-supplemented culture is compared to growth in unsupplemented medium. The extent of growth may be evaluated using any of the methods customarily used, including optical density ($OD_{600}$), $CO_2$ production, $O_2$ consumption, ATP, fluorescence, bioluminescence, manual or automated colony counts on culture plates and impedance of an electrical field. Screening may be performed in standard cultures or in microtiter plate formats.

When it is desired to identify peptides in the library which positively or negatively affect production of a cell product, the library is screened in an assay appropriate for detection of that cell product. Again, the selected cells are first grown in appropriate culture media without peptide supplement, then subcultured in media supplemented with each of the library peptides. The screening medium may be a complex medium for the selected cell type, but is preferably a defined medium to allow evaluation of peptide effects without interference from undefined materials present in the medium. It is also preferable to optimize the base medium for protein expression prior to peptide screening, although unoptimized media may also be used. A particular goal of the present work was to identify peptides which affect β-toxin production by Clostridium perfringens. In this case, β-toxin secreted from the cell was quantitated in a sandwich ELISA assay using two mouse anti-β-toxin monoclonal antibodies followed by a goat anti-mouse IgG2A conjugated to horse radish peroxidase (HRP). Toxin was quantitated by serial dilution of the cultures and compared to toxin produced by cultures which did not contain added peptide (base media cultures). Absorbance was read at 492 nm and the $B_{50}$ values (the dilutions at which the A492 signal is 50% of the maximum signal) were calculated and averaged for replicate cultures. To obtain the total toxin production value the reciprocal of the $B_{50}$ value was multiplied by the $OD_{600}$. Toxin per cell was expressed as toxin/OD. Such ELISA assay formats are easily adapted for detection of other cell products for which monoclonal antibodies or other specific binders or ligands are available or can be generated. In addition to the sandwich ELISA assay just described, other immunoassay formats may be employed to quantify β-toxin or other products of interest. These include radioimmunoassay (RIA), direct ELISA, ELISA's using other indicating enzymes, ELISA's using fluorescent reporter molecules and flow-through assays such as those which employ surface plasmon resonance detection. In addition, in the present work the ELISA results for β-toxin were confirmed in a bioassay. This was done to confirm that any increase in beta toxin detected by immunoassay represented functional toxin. Supernatants from peptide-supplemented cultures were diluted and 0.2 mL of each dilution was inoculated into mice. Unsupplemented culture media served as a negative control. Mortality was recorded 24 hrs. after injection and the greatest dilution to produce a 50% mortality rate was used as a measure of the amount of β-toxin produced.

Several peptides which affect cell growth were identified in the initial screening of the XXAL library. GEAL (SEQ ID NO:1) enhanced growth of C. perfringens by about 40%, whereas KLAL (SEQ ID NO:2) inhibited growth substantially. SEQ ID NO:2 was so inhibitory to growth that the stage II culture did not reach 1 OD, the minimum requirement for proceeding to testing in stage III. The constituent amino acids of SEQ ID NO:1 and SEQ ID NO:2 produced no significant difference in growth as compared to the base medium alone. EKAL (SEQ ID NO:3) also substantially enhanced growth in both crude form (2× improvement in growth) and purified form (3.5× improvement in growth). ESAL (SEQ ID NO:4) was also found to enhance growth in both crude and purified form. The fact that similar results were observed with both crude and purified peptides indicates that the peptide itself, and not a minor chemical involved in peptide processing, is responsible for the effect.

Toxin production in response to the peptides in the XXAL library was evaluated using 15 hr. growth and two-point ELISA values. Toxin data was collected on 75 of the 100 peptides in this library and the number of replicates per tetramer ranged from 1–14. Total toxin ratio was calculated as the quotient of the total toxin derived for media containing test peptide divided by the base media total toxin value. It was found that VNAL (SEQ ID NO:8), SNAL (SEQ ID NO:7), DKAL (SEQ ID NO:14), and NDAL (SEQ ID NO:5) increased the total toxin ratio. LSAL (SEQ ID NO:15) did not have an effect on growth, however, it significantly inhibited toxin production.

The XXAL limited diversity library was rationally designed based on the predominant C-termini found on peptides in the best-performing hydrolysate for growth of the selected cell type. This concept can be extended to design of other libraries to be screened for peptides affecting a variety of cells. The following table illustrates the C- and/or N-termini of peptides preferred for construction of libraries to be screened for compounds which affect the growth of cells which prefer culture in the presence of hydrolysates prepared with the indicated enzyme or chemical reagent.

| Reagent | Library N-terminus | Library C-terminus |
|---|---|---|
| pepsin | | L, F, M, W or Y |
| chymotrypsin | | F, W, Y, L, M, N or E |
| trypsin | | K or R |
| cyanogen bromide | | M |
| V8 protease | | D or E |
| endoproteinase Asp-N enzyme (cleaves on the N-terminal side of D) | D | |
| Cathepsin G | | F, Y or W |
| endoproteinase Lys-C | | K |
| proteinase K | F, Y, W, L or I | |
| papain | | R or K |
| thermolysin | L, F, I, V, M or A | |
| proline peptidase | A or S | P |
| hydroxylamine | G | N |
| dilute acid | P | D |
| iodasobenzoate | | W |
| BNPS-statole | | W |
| N-chlorosuccinimide | | W |
| lysyl endoproteinase | | K |
| endoproteinase Arg-C | | R |
| asparaginyl endopeptidase | | N |

Many such defined peptide termini generated by enzymes or chemical cleavage are known in the art and may be adapted to produce the libraries and peptides of the present invention. As is known in the art, it should be noted that certain of the listed enzymes (e.g., trypsin, chymotrypsin, endoproteinase Lys-C, Lysyl endoproteinase and V8 protease) may be inhibited when proline follows the indicated amino acid.

Alternatively, a more diverse and larger library may be constucted by placing the cluster group-representative "X" amino acids in all non-C-terminal positions of the tetrapeptides (e.g., an XXXL library). Alternatively, all amino acids in a particular group (rather than just single amino acids which are representative of the group) may be placed in positions 1 and 2, or in all non-C-terminal positions of the tetrapeptide. If the letter Z is used to represent any one of the possible amino acid residues such libraries would be described as, for example, ZZAL and ZZZL. As described above, the C-terminal amino acid may be any of the residues associated with known enzymatic or chemical cleavage of proteins. These concepts can be even further extended to libraries of peptides comprising more than four amino acids or to libraries of peptides comprising termini resulting from cleavage by other enzymes or chemicals, providing even larger and more diverse peptide libraries for screening. As the library evolved from XXAL to ZZAL the following peptides were found to significantly enhance cell growth: NDAL (SEQ ID NO:5), NNAL (SEQ ID NO:6), SNAL (SEQ ID NO:7) and VNAL (SEQ ID NO:8). In contrast, peptide KKAL (SEQ ID NO:9) inhibited cell growth.

The peptides EKAL (SEQ ID NO:3) and DKAL (SEQ ID NO:14) are products of a combination of these initial two library designs. A lead found in the initial XXAL library was used to identify a lead in the ZZAL space by simply substituting one member of an amino acid group (E) with another member of the same group (D), thereby reducing the screening effort. Since the C-terminus was fixed on leucine either compound could have been rapidly scaled up by an economical concatemer strategy.

In addition, a maximum diversity pentapeptide library in which the termini were not fixed was constructed wherein all permutations of an amino acid sequence were represented by a single pentapeptide sequence. This allowed the number of candidate peptides to be reduced from 3.2 million to 42,504. All sequences containing C, R and W were then eliminated, reducing the total set to 20,349. This was done to avoid potentially labor-intensive syntheses which were not necessary to exploit this new library approach. Any remaining peptides that had the same molecular formula as another peptide in the library were also eliminated, resulting in a final total of 19,243 unique structures. Screening of this library produced the following results. FEFVG (SEQ ID NO:16) had the second highest mean of the peptides tested for total toxin production (8.79) and its effect was found to be highly reproducible over multiple experimental repetitions. Further statistical analysis of SEQ ID NO:16 demonstrated that its mean for total toxin production was statistically significantly higher than the means below 7. In optimized base medium (a defined synthetic medium which does not contain hydrolysate), SEQ ID NO:16 enhanced growth by about 40% as compared to the optimized base medium alone, while addition of its constituent amino acids to the medium (F, E, V, G) increased growth only about 15%. SEQ ID NO:16 increased total toxin in the two-point ELISA by about 2.2× over total toxin production in the optimized base medium alone, while addition of the constituent amino acids resulted in total toxin production approximately equivalent to the base medium alone. It was also found that in commercial media containing 3.5% hydrolysate blend, SEQ ID NO:16 doubled the amount of toxin produced per cell but did not increase growth. This accounted for a near doubling of total toxin produced by the culture with little or no increase in cell number. This is a particularly desirable outcome for pharmaceutical companies, as the increase in toxin is obtained without the need to process additional cell mass.

The ten pentamers with the highest mean total toxin production were FSLLE (SEQ ID NO:17, 8.855), FEFVG (SEQ ID NO:16, 8.786611), FSFVE (SEQ ID NO:18, 8.727), NEYLY (SEQ ID NO:19, 8.665), FDIST (SEQ ID NO:20, 8.395), NLTEL (SEQ ID NO:21, 8.321), SQLEL (SEQ ID NO:22, 8.28375), ETLNL (SEQ ID NO:23, 8.28), NQLEV (SEQ ID NO:24, 7.81) and IKLAS (SEQ ID NO:25, 7.7475). HTVEL (SEQ ID NO:26), QNDVY (SEQ ID NO:27), LPDLF (SEQ ID NO:28), DTHHI (SEQ ID NO:29), FVPEK (SEQ ID NO:30), GYPEV (SEQ ID NO:31), HAPAY (SEQ ID NO:32), SNGIY (SEQ ID NO:33), KFIEK (SEQ ID NO:34), MHAPP (SEQ ID NO:35), MPNNF (SEQ ID NO:36), PELME (SEQ ID NO:37), FMSTA (SEQ ID NO:38), VNVQA (SEQ ID NO:39), KFIFE (SEQ ID NO:40), PLFEQ (SEQ ID NO:41), MMELE (SEQ ID NO:42), ALFHE (SEQ ID NO:43), YEQQN (SEQ ID NO:44), GGMPG (SEQ ID NO:45), SYIME (SEQ ID NO:46) and YEYIY (SEQ ID NO:47) also increased toxin per cell above the mean, as did VDLLG (SEQ ID NO:48), DMLQT (SEQ ID NO:49), GHPVE (SEQ ID NO:50), NEGLG (SEQ ID NO:51), YENLY (SEQ ID NO:52), KPLDV (SEQ ID NO:53), DKTNG (SEQ ID NO:54), EKALE (SEQ ID NO:55), SVMEM (SEQ ID NO:56), LADTF (SEQ ID NO:57), KTVGI (SEQ ID NO:58), ESLQM (SEQ ID NO:59), VEFTN (SEQ ID NO:60), ELSPH (SEQ ID NO:61), TKPFF (SEQ ID NO:62), LSFIE (SEQ ID NO:63), FEFGV (SEQ ID NO:64), GDYVS (SEQ ID NO:65), ETVNF (SEQ ID NO:66). VHVYQ (SEQ ID NO:67) and NNNNN (SEQ ID NO:68) resulted in toxin production above the mean obtained in 0.5% hydrolysate media. YEYIG (SEQ ID NO:69) in 0.5% hydrolysate media produced a total toxin mean value greater than twice that obtained using 3.5% hydrolysate alone. Pentamers AGKAH (SEQ ID NO:70), AKHSK (SEQ ID NO:71), ATNKK (SEQ ID NO:72) and ADPKD (SEQ ID NO:73) also significantly inhibited growth.

Peptides identified in the XXXX library space were also found to inhibit growth of *C. perfringens*. SKKA (SEQ ID NO:10), KGLK (SEQ ID NO:11), VKKG (SEQ ID NO:12) and GLKK (SEQ ID NO: 13).

The pentamer FEFVG (SEQ ID NO:16) was modified to form the hexamers EFEFVG (SEQ ID NO:74), NFEFVG (SEQ ID NO:75), FEFVGG (SEQ ID NO:76), FEFVGE (SEQ ID NO:77) and FEFVGY (SEQ ID NO:78), which produced total toxin values ranging from 6 to 9.7 as compared to the base media alone which had a mean total toxin of 3.82.

Cell growth in chemically defined media is typically slower than in hydrolysate based media. Several peptides were found to enhance growth in chemically defined base media sufficiently to equal growth in traditional hydrolysate based media. These peptides include VFTDK (SEQ ID NO:79), LTKVD (SEQ ID NO:80), LLPKT (SEQ ID NO:81), PLTGG (SEQ ID NO:82), GGTPV (SEQ ID NO:83), PKGTV (SEQ ID NO:84), DDDDD (SEQ ID NO:85), KLGVK (SEQ ID NO:86), TPKTL (SEQ ID NO:87), GDVTK (SEQ ID NO:88), HPAFE (SEQ ID NO:89), FFPTD (SEQ ID NO:90), VNYQA (SEQ ID NO:91) and IILEA (SEQ ID NO:92) which all produced mean growth values of 4 at 4 hours. The chemically defined screening media alone had a mean of 3.2 OD for growth at 4 hours. ESALD (SEQ ID NO:93) also enhanced growth over the base media.

Peptides identified as having the desired properties may be produced by a variety of methods in quantities sufficient for commercial or research use. The peptides may be chemically or enzymatically synthesized as is known in the art, however, more preferably the peptides are produced using methods for expression of recombinant nucleic acids encoding the peptides. For recombinant production, the selected peptide sequence is first converted to a corresponding nucleic acid sequence which encodes the amino acid sequence of the peptide. This may be an RNA sequence which is subsequently translated to produce the peptide, or it may be a DNA sequence which is then cloned into an expression vector under the control of a promoter which enables the transcription of the DNA sequence with subsequent translation of the mRNA. Many such methods for recombinant production of a desired peptide or protein sequence are well-known to the practitioner and may be applied to production of the peptides of the invention without the exercise of inventive skill. The peptides may be purified, if necessary, also using standard methods for physical, chemical and affinity separation which are well-known to the practitioner.

It is a particularly advantageous feature of many of the peptides of the invention that they comprise C-termini or N-termini corresponding to the C-termini and N-termini produced by enzymatic or chemical cleavage of proteins in traditional culture media hydrolysates. This facilitates recombinant production of the peptides, typically in bacteria or yeast, using concatemer constructs as are known in the art. Concatemers may contain hundreds of copies of the coding sequence. Concatemer nucleic acid constructs encoding peptides of the invention with C-termini or N-termini which are subject to enzymatic or chemical cleavage produce polypeptides comprising repeating subunits of the peptide amino acid sequence separated by convenient cleavage sites. Cleavage using the appropriate enzymatic or chemical means releases the peptide monomer. This approach to manufacture increases the yield of the desired peptide and decreases manufacturing costs. Post-expression processing is simplified due to the cleavage site which is automatically produced by cloning of the concatamer structure. For example, the peptide NDAL (SEQ ID NO:5) was quickly discovered using the XXAL library approach and can be efficiently manufactured using the concatamer strategy with subsequent cleavage using pepsin or the endopeptidase N-ASN. The growth inhibitor KKAL (SEQ ID NO:9) could also be manufactured using the concatamer strategy and cleavage with pepsin. FSFVE (SEQ ID NO:18) could be expressed as a concatamer and cleaved into monomers following expression using the V8 protease. As a further example, HTVEL (SEQ ID NO:26) and QNDVY (SEQ ID NO:27) both enhance beta toxin accumulation in the culture supernatant. These peptides could be expressed from the same concatamer minigene, cleaved by pepsin into peptides and used without further separation since both exhibit the same attribute. Such a combination minigene may also be useful when one peptide is needed to balance another. For example, alternating a basic sequence with an acidic sequence may make the total minigene product compatible with the host cell. Combination minigenes may also be useful production vehicles when multiple peptides exhibiting different attributes are desired for formulation into the same medium. In this case, all the necessary peptides may be expressed, processed and formulated in a single production process without the need to separate the individual peptides.

FEFVG (SEQ ID NO:16) can be cloned as a concatamer with a nonsense sequence spacer between each peptide coding sequence to permit liberation from the concatamer. For example, the coding sequence for the nonsense peptide DEEP (SEQ ID NO:94) could flank the sequence coding for the media enhancer peptide, and the concatamer could be cleaved with the endoproteinase Asp-N (which cuts before aspartic acid) and proline endopeptidase (which cuts after proline). This approach requires multiple reagents and the spacer may need to be separated from the desired peptide if it is not compatible with the cell culture. Nonsense spacers may also be used between peptide coding sequences in the concatemer to generate cleavable sites and facilitate processing in otherwise non-cleavable peptide sequences.

The preferred use of the peptides of the invention is in cell culture media (including media for culture of cells and tissues derived from prokaryotes and eukaryotes, vertebrates and invertebrates) to produce a desired effect on the cells. Such effects may include increased or decreased growth rate, increased or decreased production of a cell product, or increased or decreased response to a substance in the environment (e.g., a hormone). The base culture medium to which the peptide is added may be a chemically defined medium or a complex medium containing undefined components such as fetal calf serum (FCS) or yeast hydrolysate. Chemically defined or semi-defined media are preferred, as the peptides of the invention are most advantageously used as a means for reducing or eliminating performance variability due to undefined media components and for reducing or eliminating animal-derived components in media used to produce pharmaceutical products.

A selected peptide is typically added to the culture medium at a concentration from about 0.1–25 mM more preferably from about 1.0 and 12 mM. However, it is within the ordinary skill in the art to determine an appropriate concentration of an inventive peptide in a selected culture medium. Multiple peptides may be added to the culture medium to produce a synergistic effect (if both have the same effect on the cells) or to produce multiple effects (if each peptide has a different effect on the cells).

The invention claimed is:

1. A method for enhancing cell growth or cellular protein production comprising culturing cells or tissues in the presence of a peptide having an amino acid sequence consisting of an amino acid sequence selected from the group consisting of FEFVG (SEQ ID NO:16), FSLLE (SEQ ID NO:17), FSFVE (SEQ ID NO:18), NEYLY (SEQ ID NO:19), FDIST (SEQ ID NO:20), NLTEL (SEQ ID NO:21), SQLEL (SEQ ID NO:22), ETLNL (SEQ ID NO:23), NOLEV (SEQ ID NO:24), and IKLAS (SEQ ID NO:25).

2. The method of claim 1 wherein growth of *C. Perfringens* is enhanced.

3. The method of claim 1 wherein production of β-toxin is enhanced.

4. The method or claim 1 wherein the cells are cultured in the presence of about 0.1–25 mM of the peptide.

5. The method of claim 4 wherein the cells are cultured in the presence of about 1.0–12 mM of the peptide.

6. The method of claim 1 wherein said peptide is FEFVG (SEQ ID NO:16 and wherein cell growth and cellular protein production are enhanced.

7. The method of claim 1, wherein said peptide is FSLLE (SEQ TD NO:17) and wherein cellular protein production is enhanced.

8. The method of claim 1, wherein said peptide is FSFVE (SEQ ID NO:18) and wherein cellular protein production is enhanced.

9. The method of claim 1, wherein said peptide is NEYLY (SEQ ID NO:19) and wherein cellular protein production is enhanced.

10. The method of claim 1, wherein said peptide is FDIST (SEQ ID NO:20) and wherein cellular protein production is enhanced.

11. The method of claim 1, wherein said peptide is NLTEL (SEQ ID NO:21) and wherein cellular protein production is enhanced.

12. The method of claim 1, wherein said peptide is SQLEL (SEQ ID NO:22) and wherein cellular protein production is enhanced.

13. The method of claim 1, wherein said peptide is ETLNL (SEQ ID NO:23) and wherein cellular protein production is enhanced.

14. The method of claim 1, wherein said peptide is NOLEV (SEQ ID NO:24) and wherein cellular protein production is enhanced.

15. The method of claim 1, wherein said peptide is IKLAS (SEQ ID NO:25) and wherein cellular protein production is enhanced.

* * * * *

SEQUENCE LISTING

```
<160> NUMBER OF SEQ ID NOS: 94

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 1

Gly Glu Ala Leu
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:Synthetic
```

-continued

```
              peptide selected for biological activity

<400> SEQUENCE: 2

Lys Leu Ala Leu
  1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 3

Glu Lys Ala Leu
  1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 4

Glu Ser Ala Leu
  1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 5

Asn Asp Ala Leu
  1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 6

Asn Asn Ala Leu
  1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 7

Ser Asn Ala Leu
  1

<210> SEQ ID NO 8
```

```
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 8

Val Asn Ala Leu
  1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 9

Lys Lys Ala Leu
  1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 10

Ser Lys Lys Ala
  1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 11

Lys Gly Leu Lys
  1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 12

Val Lys Lys Gly
  1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 13
```

```
Gly Leu Lys Lys
 1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 14

Asp Lys Ala Leu
 1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 15

Leu Ser Ala Leu
 1

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 16

Phe Glu Phe Val Gly
 1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 17

Phe Ser Leu Leu Glu
 1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 18

Phe Ser Phe Val Glu
 1               5

<210> SEQ ID NO 19
<211> LENGTH: 5
<212> TYPE: PRT
<213> ORGANISM: Artificial Sequence
<220> FEATURE:
```

-continued

<223> OTHER INFORMATION: Description of Artificial Sequence:Synthetic
      peptide selected for biological activity

<400> SEQUENCE: 19

Asn Glu Tyr Leu Tyr
 1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 20

Phe Asp Ile Ser Thr
 1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 21

Asn Leu Thr Glu Leu
 1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 22

Ser Gln Leu Glu Leu
 1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 23

Glu Thr Leu Asn Leu
 1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 24

Asn Gln Leu Glu Val
 1               5

-continued

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 25

Ile Lys Leu Ala Ser
 1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 26

His Thr Val Glu Leu
 1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 27

Gln Asn Asp Val Tyr
 1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 28

Leu Pro Asp Leu Phe
 1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 29

Asp Thr His His Ile
 1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 30

```
Phe Val Pro Glu Lys
  1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 31

Gly Tyr Pro Glu Val
  1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 32

His Ala Pro Ala Tyr
  1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 33

Ser Asn Gly Ile Tyr
  1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 34

Lys Phe Ile Glu Lys
  1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 35

Met His Ala Pro Pro
  1               5

<210> SEQ ID NO 36
<211> LENGTH: 5
<212> TYPE: PRT
<213> ORGANISM: Artificial Sequence
```

```
<220> FEATURE:
<223> OTHER INFORMATION: Description of Artificial Sequence:Synthetic
      peptide selected for biological activity

<400> SEQUENCE: 36

Met Pro Asn Asn Phe
 1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 37

Pro Glu Leu Met Glu
 1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 38

Phe Met Ser Thr Ala
 1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 39

Val Asn Val Gln Ala
 1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 40

Lys Phe Ile Phe Glu
 1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 41

Pro Leu Phe Glu Gln
 1               5
```

```
<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 42

Met Met Glu Leu Glu
  1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 43

Ala Leu Phe His Glu
  1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 44

Tyr Glu Gln Gln Asn
  1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 45

Gly Gly Met Pro Gly
  1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 46

Ser Tyr Ile Met Glu
  1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity
```

```
<400> SEQUENCE: 47

Tyr Glu Tyr Ile Tyr
 1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 48

Val Asp Leu Leu Gly
 1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 49

Asp Met Leu Gln Thr
 1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 50

Gly His Pro Val Glu
 1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 51

Asn Glu Gly Leu Gly
 1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 52

Tyr Glu Asn Leu Tyr
 1               5

<210> SEQ ID NO 53
<211> LENGTH: 5
<212> TYPE: PRT
```

```
<213> ORGANISM: Artificial Sequence
<220> FEATURE:
<223> OTHER INFORMATION: Description of Artificial Sequence:Synthetic
      peptide selected for biological activity

<400> SEQUENCE: 53

Lys Pro Leu Asp Val
  1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 54

Asp Lys Thr Asn Gly
  1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 55

Glu Lys Ala Leu Glu
  1               5

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 56

Ser Val Met Glu Met
  1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 57

Leu Ala Asp Thr Phe
  1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 58

Lys Thr Val Gly Ile
  1               5
```

```
<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 59

Glu Ser Leu Gln Met
 1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 60

Val Glu Phe Thr Asn
 1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 61

Glu Leu Ser Pro His
 1               5

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 62

Thr Lys Pro Phe Phe
 1               5

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 63

Leu Ser Phe Ile Glu
 1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity
```

```
<400> SEQUENCE: 64

Phe Glu Phe Gly Val
  1               5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 65

Gly Asp Tyr Val Ser
  1               5

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 66

Glu Thr Val Asn Phe
  1               5

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 67

Val His Val Tyr Gln
  1               5

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 68

Asn Asn Asn Asn Asn
  1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 69

Tyr Glu Tyr Ile Gly
  1               5

<210> SEQ ID NO 70
<211> LENGTH: 5
```

```
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 70

Ala Gly Lys Ala His
 1               5

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 71

Ala Lys His Ser Lys
 1               5

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 72

Ala Thr Asn Lys Lys
 1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 73

Ala Asp Pro Lys Asp
 1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 74

Glu Phe Glu Phe Val Gly
 1               5

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 75

Asn Phe Glu Phe Val Gly
```

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence:Synthetic peptide selected for biological activity

<400> SEQUENCE: 76

Phe Glu Phe Val Gly Gly
 1               5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence:Synthetic peptide selected for biological activity

<400> SEQUENCE: 77

Phe Glu Phe Val Gly Glu
 1               5

<210> SEQ ID NO 78
<211> LENGTH: 6
<212> TYPE: PRT
<213> ORGANISM: Artificial Sequence
<220> FEATURE:
<223> OTHER INFORMATION: Description of Artificial Sequence:Synthetic peptide selected for biological activity

<400> SEQUENCE: 78

Phe Glu Phe Val Gly Tyr
 1               5

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence:Synthetic peptide selected for biological activity

<400> SEQUENCE: 79

Val Phe Thr Asp Lys
 1               5

<210> SEQ ID NO 80
<211> LENGTH: 5
<212> TYPE: PRT
<213> ORGANISM: Artificial Sequence
<220> FEATURE:
<223> OTHER INFORMATION: Description of Artificial Sequence:Synthetic peptide selected for biological activity

<400> SEQUENCE: 80

Leu Thr Lys Val Asp
 1               5

<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence:Synthetic peptide selected for biological activity

<400> SEQUENCE: 81

Leu Leu Pro Lys Thr
 1               5

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 82

Pro Leu Thr Gly Gly
 1               5

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 83

Gly Gly Thr Pro Val
 1               5

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 84

Pro Lys Gly Thr Val
 1               5

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 85

Asp Asp Asp Asp Asp
 1               5

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 86

Lys Leu Gly Val Lys
 1               5

<210> SEQ ID NO 87

```
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 87

Thr Pro Lys Thr Leu
 1               5

<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 88

Gly Asp Val Thr Lys
 1               5

<210> SEQ ID NO 89
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 89

His Pro Ala Phe Glu
 1               5

<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 90

Phe Phe Pro Thr Asp
 1               5

<210> SEQ ID NO 91
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 91

Val Asn Tyr Gln Ala
 1               5

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 92
```

-continued

```
Ile Ile Leu Glu Ala
  1             5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide selected for biological activity

<400> SEQUENCE: 93

Glu Ser Ala Leu Asp
  1             5

<210> SEQ ID NO 94
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide linker

<400> SEQUENCE: 94

Asp Glu Glu Pro
  1
```